(12) United States Patent
Mujwid et al.

(10) Patent No.: US 10,398,431 B2
(45) Date of Patent: Sep. 3, 2019

(54) SURGICAL NEEDLE AND ANCHOR SYSTEM WITH RETRACTABLE FEATURES

(71) Applicant: Boston Scientific Scimed, Inc., Maple Grove, MN (US)

(72) Inventors: James R. Mujwid, Crystal, MN (US); Kory P. Hamel, Bloomington, MN (US); James A. Alexander, Excelsior, MN (US); John J. Buysman, Minnetonka, MN (US); John F. Otte, St. Anthony, MN (US); Jason W. Ogdahl, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 288 days.

(21) Appl. No.: 14/811,826

(22) Filed: Jul. 28, 2015

(65) Prior Publication Data

US 2015/0327971 A1 Nov. 19, 2015

Related U.S. Application Data

(63) Continuation of application No. 13/846,139, filed on Mar. 18, 2013, which is a continuation of application
(Continued)

(51) Int. Cl.
*A61F 2/00* (2006.01)
*A61B 17/00* (2006.01)
(Continued)

(52) U.S. Cl.
CPC .... *A61B 17/06109* (2013.01); *A61B 17/0401* (2013.01); *A61B 17/3476* (2013.01);
(Continued)

(58) Field of Classification Search
CPC .................. A61F 2/0004; A61F 2/0045; A61F 2002/0072; A61B 2017/0401–0462; A61B 2017/06109
See application file for complete search history.

(56) References Cited

U.S. PATENT DOCUMENTS

| 728,786 A | 5/1903 | Villeneuve |
| D444,557 S | 7/2001 | Levaughn et al. |

(Continued)

FOREIGN PATENT DOCUMENTS

| WO | 2004017845 A1 | 3/2004 |
| WO | 2007097994 A2 | 8/2007 |

(Continued)

OTHER PUBLICATIONS

First Examination Report for Australian Application No. 2015203295, dated May 3, 2017, 3 pages.

(Continued)

*Primary Examiner* — Catherine B Kuhlman
(74) *Attorney, Agent, or Firm* — Brake Hughes Bellermann LLP

(57) ABSTRACT

Various surgical introducer needle and anchor systems are provided. The systems can include an introducer needle and a tissue support implant or sling device. The implant device can include one or more anchoring devices. The introducer needle device can include a handle assembly and a needle assembly. The needle assembly can include a generally hollow needle, and a wire traversable therein. The wire can include a distal tip adapted to selectively retract or withdraw from the engaged anchoring device upon deployment of the anchor and/or implant.

19 Claims, 21 Drawing Sheets

Related U.S. Application Data

No. 12/606,758, filed on Oct. 27, 2009, now Pat. No. 8,944,990.

(60) Provisional application No. 61/108,686, filed on Oct. 27, 2008, provisional application No. 61/173,396, filed on Apr. 28, 2009, provisional application No. 61/186,616, filed on Jun. 12, 2009.

(51) Int. Cl.
  *A61B 17/06* (2006.01)
  *A61B 17/04* (2006.01)
  *A61B 17/34* (2006.01)
(52) U.S. Cl.
  CPC .......... *A61F 2/0045* (2013.01); *A61F 2/0063* (2013.01); *A61B 2017/00805* (2013.01); *A61B 2017/0409* (2013.01); *A61B 2017/0412* (2013.01); *A61B 2017/0445* (2013.01); *A61F 2002/0072* (2013.01)

(56) References Cited

U.S. PATENT DOCUMENTS

| | | | |
|---|---|---|---|
| 6,355,017 | B2 | 3/2002 | Buttgen et al. |
| 6,691,711 | B2 | 2/2004 | Raz et al. |
| D499,182 | S | 11/2004 | Moore et al. |
| D525,361 | S | 7/2006 | Hushka |
| 7,351,197 | B2 | 4/2008 | Montpetit et al. |
| D569,515 | S | 5/2008 | DeLonzor et al. |
| D569,516 | S | 5/2008 | DeLonzor et al. |
| D575,395 | S | 8/2008 | Hushka |
| D585,547 | S | 1/2009 | Bisleri |
| D628,290 | S | 11/2010 | Romero |
| D628,695 | S | 12/2010 | Ruf |
| D634,426 | S | 3/2011 | Zollers |
| 8,070,672 | B2 | 12/2011 | Rehder et al. |
| D659,828 | S | 5/2012 | Horning et al. |
| D660,430 | S | 5/2012 | Horning et al. |
| D662,206 | S | 6/2012 | Way et al. |
| D665,909 | S | 8/2012 | Dodd et al. |
| D671,644 | S | 11/2012 | Dodd et al. |
| D673,679 | S | 1/2013 | Hong |
| D733,298 | S | 6/2015 | Mujwid et al. |
| 2002/0055748 | A1 | 5/2002 | Gellman et al. |
| 2002/0147382 | A1 | 10/2002 | Neisz et al. |
| 2002/0151762 | A1 | 10/2002 | Rocheleau et al. |
| 2002/0151909 | A1 | 10/2002 | Gellman et al. |
| 2002/0161382 | A1* | 10/2002 | Neisz ................. A61B 17/0644 606/151 |
| 2003/0023250 | A1* | 1/2003 | Watschke ........... A61B 17/0469 606/148 |
| 2003/0120287 | A1 | 6/2003 | Gross et al. |
| 2003/0191360 | A1 | 10/2003 | Browning |
| 2004/0039302 | A1 | 2/2004 | Kim |
| 2004/0122474 | A1* | 6/2004 | Gellman ............ A61B 17/0401 606/232 |
| 2004/0162573 | A1 | 8/2004 | Kheiri |
| 2005/0256530 | A1* | 11/2005 | Petros ................ A61B 17/0401 606/151 |
| 2005/0283246 | A1 | 12/2005 | Cauthen et al. |
| 2006/0004364 | A1 | 1/2006 | Green et al. |
| 2008/0004651 | A1 | 1/2008 | Nicholls et al. |
| 2008/0039885 | A1 | 2/2008 | Purcell |
| 2008/0058631 | A1 | 3/2008 | Draudt et al. |
| 2009/0036903 | A1 | 2/2009 | Ino et al. |
| 2009/0105750 | A1 | 4/2009 | Price et al. |
| 2009/0221868 | A1* | 9/2009 | Evans .................. A61F 2/0045 600/37 |
| 2011/0160529 | A1* | 6/2011 | Crawford ............. A61F 2/0045 600/37 |
| 2015/0327971 | A1 | 11/2015 | Mujwid et al. |

FOREIGN PATENT DOCUMENTS

| | | | |
|---|---|---|---|
| WO | 2008057261 | A2 | 5/2008 |
| WO | 2009017680 | A2 | 2/2009 |

OTHER PUBLICATIONS

Office Action for European Application No. 09747962.0, dated Mar. 10, 2017, 4 pages.
Response to First Examiner's Report for Australian Application No. 2015203295, filed Mar. 15, 2018, 14 pages.
Extended European Search Report for European Application No. 18178408.3, dated Nov. 15, 2018, 7 pages.

\* cited by examiner

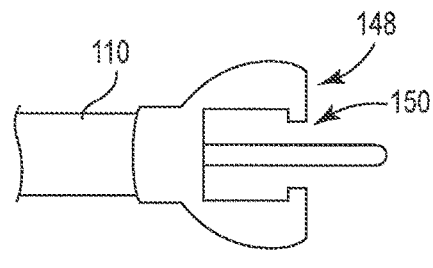 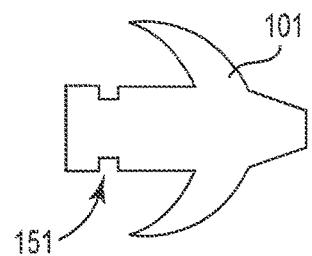
Fig. 29a    Fig. 29b
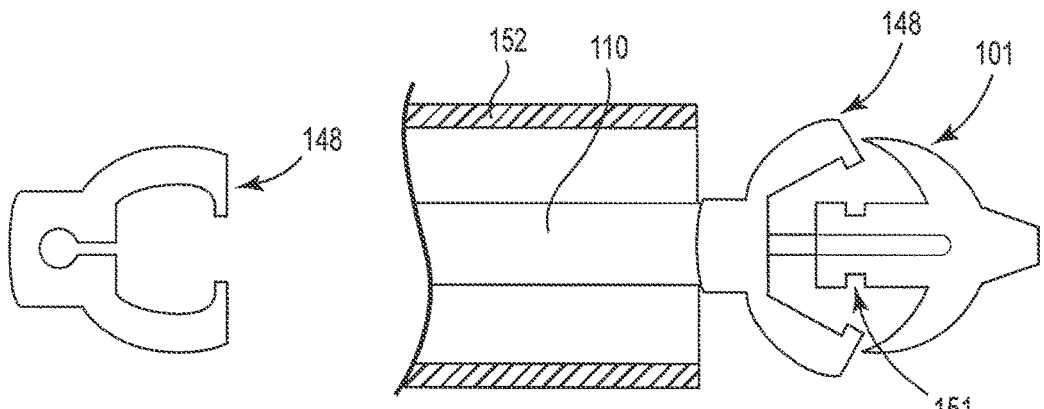
Fig. 30    Fig. 31a
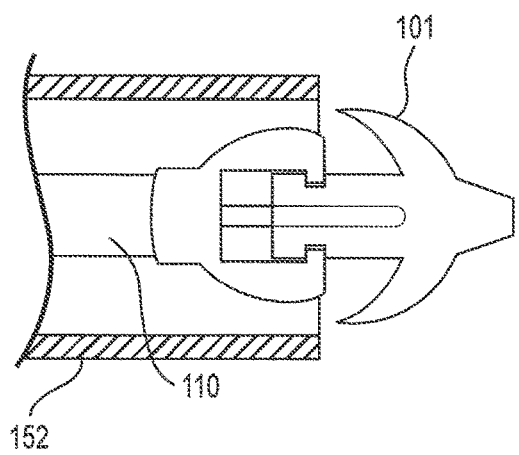
Fig. 31b

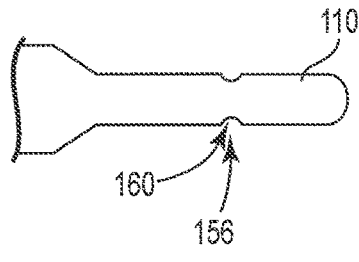
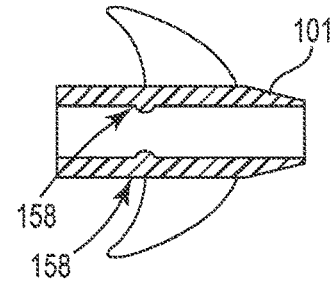
Fig. 32a     Fig. 32b
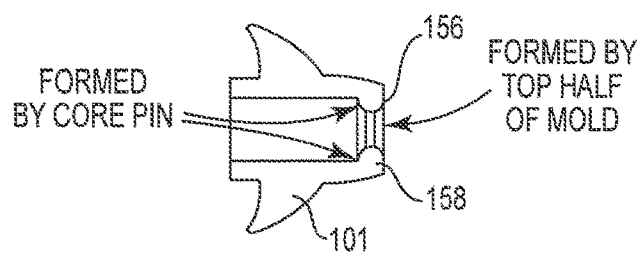
Fig. 32c
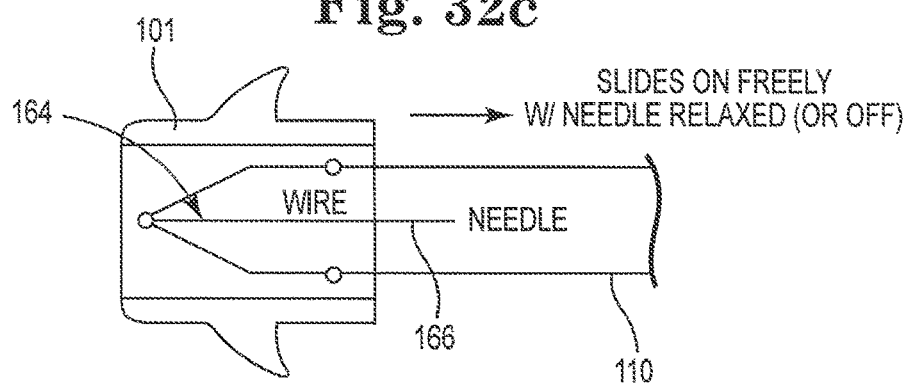
Fig. 33
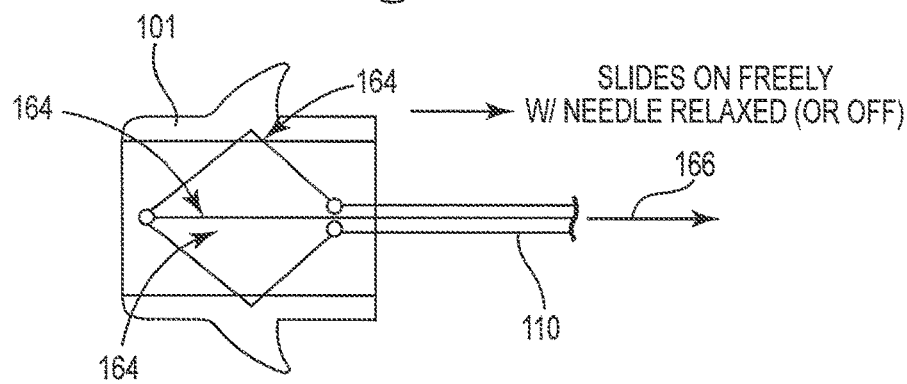
Fig. 34

SURGICAL NEEDLE AND ANCHOR SYSTEM WITH RETRACTABLE FEATURES

RELATED APPLICATIONS

This application claims priority to and is a Continuation Application of U.S. patent application Ser. No. 13/846,139, filed Mar. 18, 2013, which is a Continuation Application of U.S. patent application Ser. No. 12/606,758, filed Oct. 27, 2009, which claims priority to and the benefit of U.S. Provisional Application No. 61/108,686 filed Oct. 27, 2008, U.S. Provisional Application No. 61/173,396 filed Apr. 28, 2009, and U.S. Provisional Application No. 61/186,616 filed Jun. 12, 2009, with each of the above-referenced applications and disclosures incorporated fully herein by reference in their entirety.

FIELD OF THE INVENTION

The present invention relates generally to surgical methods and apparatus and, more specifically, to a surgical needle adapted to selectively engage one or more implant anchors, such as those used for anchoring to soft tissue.

BACKGROUND OF THE INVENTION

Pelvic health for men and women is a medical area of increasing importance, at least in part due to an aging population. Examples of common pelvic ailments include incontinence (fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

A specific area of pelvic health is trauma of the pelvic floor, e.g., of the levator ("levator ani") or coccygeus muscle (collectively the pelvic floor). The pelvic floor is made up of the levator and coccygeus muscles, and the levator is made up of components that include the puborectalis muscle, the pubococcygeus muscle, and the iliococcygeous muscle. For various reasons, the levator may suffer weakness or injury such as damage to the levator hiatus, ballooning or levator avulsion, any of which that can result in symptoms such as prolapse, fecal incontinence, and other conditions of the pelvis.

Levator defects (weakness or injury) can affect any portion of the levator, and can be especially common in the pubic portion of the levator ani, including the pubococcygeus and puborectalis muscles. Such defects are relatively common, for instance, in women with vaginal prolapse. Defects can also be present at the iliococcygeus muscle. Still other defects are in the form of a paravaginal defect, such as avulsion of the inferiomedial aspects of the levator ani from the pelvic sidewall; avulsion can refer to tissue being detached from the pubic bone, and may precede prolapse conditions. Another levator defect is levator ballooning, which refers to distension of levator muscles.

A different levator defect is a defect of the levator hiatus, which can reduce the stability of the pelvic floor and may result in sexual dysfunction, defecatory dysfunction, rectal prolapse, and fecal incontinence. Levator hiatus is also believed to play a significant role in the progression of prolapse.

There is a desire to obtain a minimally invasive yet highly effective needle and anchoring system that can be used to treat incontinence, pelvic organ prolapse and other conditions.

SUMMARY OF THE INVENTION

In one embodiment, a surgical introducer needle and anchor kit or system includes an implantable support apparatus, such as a sling, mesh or straps, a needle assembly having a retractable wire and handle assembly, and one or more anchoring devices generally attached at one or more ends of the support apparatus. Each anchor device is adapted for attachment to tissue within the pelvis of a patient such that attachment to the patient tissue allows for selective placement of the support apparatus to support the patient's bladder, urethra or other organs or tissue. The handle and needle assemblies are adapted to operatively and selectively engage and direct the anchors and support apparatus of the system.

The needle and anchoring assemblies can be configured to provide increased precision, reliability and usefulness in engaging an anchor device or implant, and retracting the needle, or a portion thereof, from the anchor upon deployment. Various embodiments of the needle system of the present invention can include a handle operatively coupled with a cannulated needle and an internal wire or like structure such that a distal tip of the wire is selectively engageable with and retractable from the implant or anchor. The internal wire and the respective distal tip can be retractable within the needle by way of at least one actuator, e.g., a slider actuator.

Other embodiments of the handle assembly can include a lock-out assembly to limit back travel of the wire distal tip during deployment, with the tip being capable of retraction upon use of the at least one actuator.

Still other embodiments of the handle assembly can include a clicker or toggle mechanism as the at least one actuator to selectively toggle retraction and extension of the wire distal tip.

Various anchor systems can be included to provide security so that the anchor will not easily detach or disengage from the needle during insertion, while still allowing for accurate placement and detachment of the anchor from the needle during deployment of the anchor e.g., within soft tissue within the pelvic region of a patient. For instance, retraction of the needle, or a portion thereof, from the anchor promotes stable and accurate positioning because the anchor is not forced or pushed off of the needle device (causing positional movement or shifting of the anchor). Instead, the anchor is securely seated in abutable contact with the needle (e.g., the barb guard) such that retraction of the needle or wire does not generally alter the angle, positioning or location of the anchor.

BRIEF DESCRIPTION OF THE DRAWINGS

FIGS. 29a-31b are schematic views of a locking barb needle and anchor system in accordance with embodiments of the present invention.

FIGS. 32a-32c are schematic views of a snap fit needle and anchor system in accordance with embodiments of the present invention.

FIGS. 33-34 are schematic views of a squeeze lock needle and anchor system in accordance with embodiments of the present invention.

DETAILED DESCRIPTION OF PREFERRED EMBODIMENTS

Figure 1:
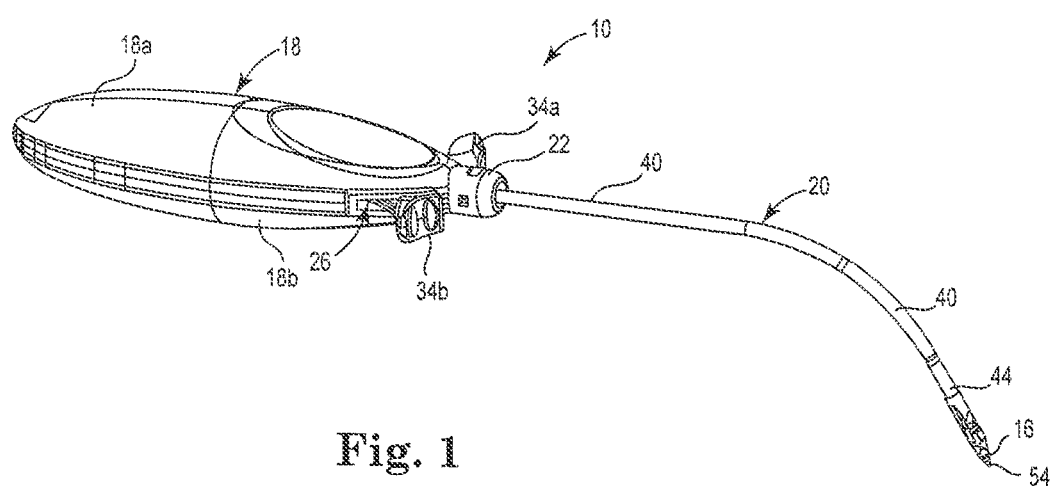
FIG. 1 is a perspective view of a surgical introducer needle and anchor system in accordance with embodiments of the present invention.
Figure 2:
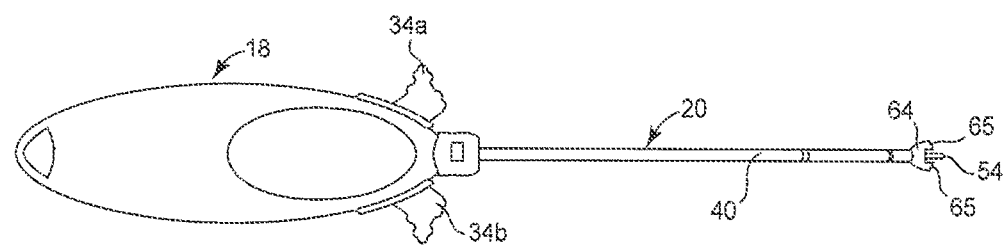
FIG. 2 is a top view of a surgical introducer needle and anchor system in accordance with embodiments of the present invention.

Referring generally to FIGS. 1-21, various embodiments of surgical introducer needle and anchor systems 10 are shown. In general, the systems 10 can include a needle device and a tissue support implant or sling device. The implant device can include one or more anchoring devices. The anchoring devices can be referred to as self-fixating anchors or tips. The introducer needle device can include a handle assembly 18 and a needle assembly 20. The systems 10 can be adapted for use to anchor implants in females to support tissue to treat incontinence, prolapse or other pelvic health conditions. The present invention may be used to correct central defects, midline defects, both midline and central defects at once, as well as other like conditions. Further, the various components of the systems 10 can be constructed of materials such as polymers, metals, and other like materials compatible for use with surgical needle, handle, and anchor devices and systems as known to one of ordinary skill in the art.

The various systems 10, features and methods detailed herein are envisioned for use with many known implant and repair systems (e.g., for male and female), features and methods, including those disclosed in U.S. Pat. Nos. 7,351, 197 and 6,691,711, International Patent Publication Nos. WO 2008/057261 and WO 2007/097994, U.S. Patent Publication Nos. 2002/151762 and 2002/147382, and International Patent Application Serial No. PCT/US2008/009066, filed Jul. 25, 2008. Accordingly, the above-identified disclosures are incorporated herein by reference in their entirety.

Referring generally to FIGS. 1-18, embodiments of the handle assembly 18 and the retractable needle assembly 20 are shown. The handle 18 can be provided in a clam-shell configuration, and can be constructed of polymer materials, metals and other materials known to those of ordinary skill in the art. The handle 18 can be configured to include a first portion of 18a and a second portion or 18b adapted to snap or otherwise fasten or couple to one another. Various known fastener, fitting, boss and post, and like attachment configurations and techniques can be employed to join or attach the portions 18a, 18b of the handle 18 together. The handle assembly 18 can further include one or more actuators 34, e.g., two actuator sliders 34a, 34b, which can be slid, pressed, or otherwise engaged to extend and retract at least a portion of the needle assembly 20. Disposed within a cavity or other portion of the handle assembly 18 is a biasing member 36, such as a spring. As detailed herein, the biasing member 36 biases the one or more actuators 34 in the extended position in one embodiment.

Each housing portion 18a, 18b can include a neck portion 22, and channels or recesses 24. When the housing portions 18a, 18b are coupled, the recesses 24 define openings 26 adapted to provide spacing for the actuators 34a, 34b to traverse or slide along or within, with at least a portion of the actuators 34a, 34b extending out from the openings 26. Similarly, coupling of the housing portions 18a, 18b joins the neck portions 22 to define an opening for shrouding a portion of the needle assembly 20.

Figure 6:
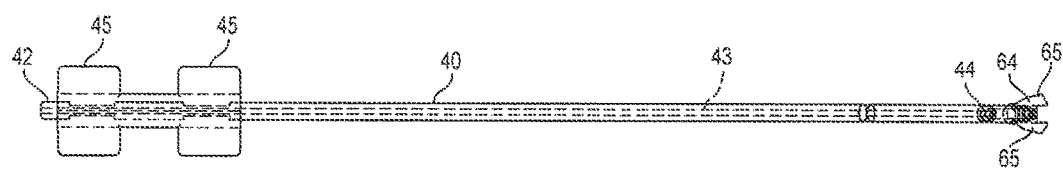
FIG. 6 is a top schematic view of a needle assembly in accordance with embodiments of the present invention.
Figure 7:
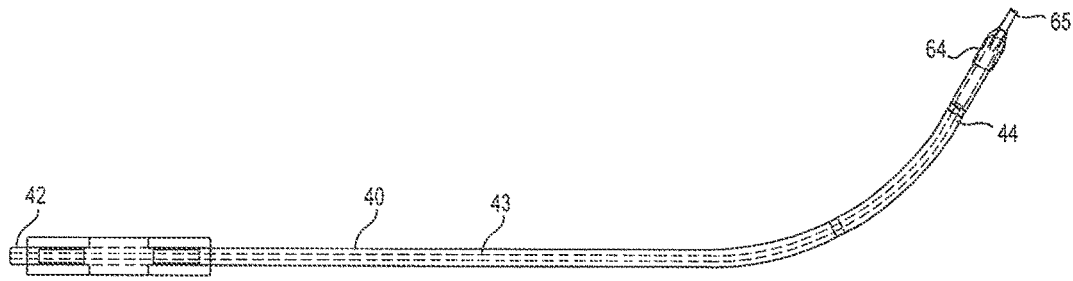
FIG. 7 is a side schematic view of a needle assembly in accordance with embodiments of the present invention.

The needle assembly 20 can include an elongate cannulated needle 40 having a proximal end 42 and an engagement tip or distal end 44, with a lumen 43 extending therethrough, as illustrated in FIGS. 6-7. The proximal end 42 is adapted for interfitting with or operatively connecting to the handle assembly 18. As such, the proximal end 42 can include an alignment portion 45, such as an alignment block, adapted to rest or otherwise align and secure the proximal end 42 within the handle assembly 18 or its components, generally maintaining the needle 40 in a stationary position during use.

In one embodiment, at least a portion of the needle 40 is generally curved or arcuate (e.g., FIGS. 1, 3 and 7) to facilitate pelvic introduction and maneuverability. The needle 40 can be configured to have an overall length of between about 4 inches and 6 inches, with a generally straight portion between 3 inches and 4 inches, and a curved portion extending the rest of the length to the distal end 44. Such a needle 40 design can have an outer diameter of about 0.07 inches to 0.10 inches, with various inner diameters envisioned for the lumen 43 (e.g., approximately 0.030 inches). However, in other embodiments the needle 40 can be generally straight along its entire length, or can take on a variation of other known shape and size configurations. The needle 40, or portions thereof, can be constructed of compatible polymers or metals, including stainless steel. Within the housing assembly 18, the proximal end 42 of the needle 40 can extend through and past the alignment portion 45, and be secured or configured to restrict rotational movement of the needle 40.

Figure 8:
FIG. 8 is a top schematic view of an actuator wire in accordance with embodiments of the present invention.
Figure 9:
FIG. 9 is a side schematic view of wire distal tip portion in accordance with embodiments of the present invention.
Figure 10:
FIG. 10 is a side schematic cross-section view of an actuator wire coupled with a distal tip portion in accordance with embodiments of the present invention.

Further, as shown in FIGS. 8-10, the needle assembly 20 can include an actuator wire 50 capable of traversing at least along a portion of the inner diameter of the needle lumen 43. The wire 50, or portions thereof, can be constructed of compatible polymers or metals, including stainless steel. The wire 50 includes a wire proximal portion 52 and a wire distal portion or tip 54. The wire proximal portion 52 is adapted to operatively interface or connect with components or structures within the handle assembly 18, such as a portion of the one or more actuators 34. In one embodiment, the wire distal portion or tip 54 can be a separate member coupled with an end of the wire 50. For instance, the distal tip 54 can be measurably larger in diameter than the wire 50 diameter, including a coupling channel or recess 54a defined therein to receive and secure the relatively thinner wire 50 (FIGS. 9-10). The wire 50 is retractable and extendable along a distance of the lumen 43 such that the wire distal portion 54 is capable of extending out of or from the distal end 44 of the needle 40 and lumen 43. In other embodiments, the wire 50 or at least a portion of the wire 50 can be disposed along or traverse the outside of the needle, such as through a sleeve external to the needle, along the outside length of the needle, through or along a lumen or structure generally separate or distinct from the needle, etc.

Figure 12:
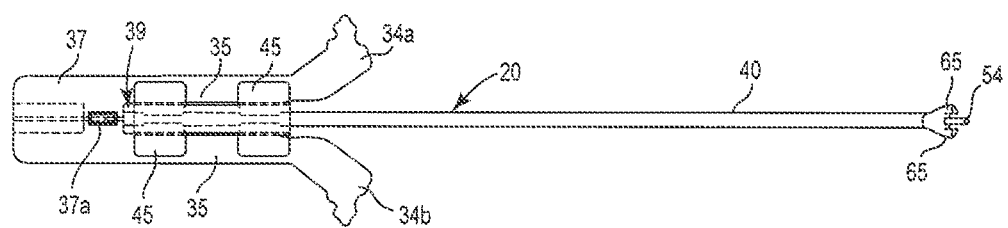
FIG. 12 is a top schematic view of a needle assembly and handle actuator in accordance with embodiments of the present invention.

As provided herein, the alignment portion 45 can be adapted to mate or couple with a portion of the proximal end 42 of the needle 40 for integration within the handle assembly 18, as shown in FIG. 12. For instance, in one embodiment, the alignment portion 45 can be generally H-shaped with a lumen 47 defined therein to receive the proximal end 42 of the needle 40. As such, receiving channels 49 can be provided within the alignment portion 45 to slidably receive portions of the actuator 34.

Figure 11:
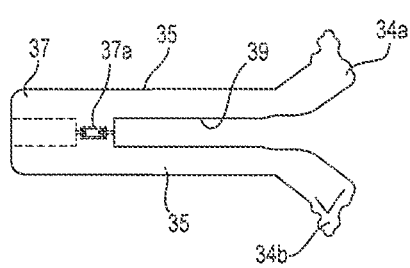
FIG. 11 is a top schematic view of a handle actuator in accordance with embodiments of the present invention.
Figure 13:
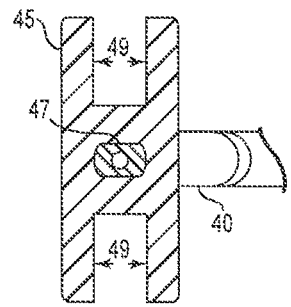
FIG. 13 is a front schematic cross-section view of an alignment portion and needle in accordance with embodiments of the present invention.

In an embodiment as depicted in FIGS. 11-13, the one or more actuators 34 can be constructed to include two actuators 34a, 34b, body portions 35, a proximal base 37, and a gap 39. The body portions 35 can extend into the housing 18 from respective actuators 34a, 34b to define the gap 39 therebetween. The proximal base 37 can be adapted to receive the proximal portion 52 of the wire 50, e.g., by crimping or otherwise securing the proximal portion 52 of the wire 50 to a portion of the proximal base 37 (FIG. 12). In one embodiment, the proximal portion 52 of the wire 50 can be crimped at a securing portion 37a of the proximal base 37. Further, the proximal base 37 can include a bore or recess therein to receive at least an end region of the biasing member 36, with the other end region abutting against one or more structures within at least one of the handle halves 18a, 18b.

The body portions 35 extending from the actuators 34a, 34b can be disposed within or extend into the corresponding receiving channels 49 of the alignment portion 45 of the needle 40 as a guiding feature, such that the respective body portions 35 can slide within the receiving channels 49, with the alignment portion 45 remaining substantially stationary. In such a configuration, the body portions 35 can slide within or along the channels 49 upon activation or engagement by an end user of the actuators 34a, 34b, while still maintaining placement and securement of the components within the handle assembly 18. Accordingly, the needle 40 is generally secured and the wire 50, coupled to the proximal base 37 (e.g., at portion 37a) of the actuators, is adapted to correspondingly travel with the actuators 34a, 34b. Other configurations and designs for the handle assembly 18, including its sliding, guiding and coupling components, can be employed as well without deviating from the spirit and scope of the invention.

Referring generally to FIGS. 4-5, and 14-16, when the actuators 34a, 34b are in an extended position, e.g., generally away from the handle assembly 18, the wire distal portion 54 is also in an extended or engageable position, e.g., generally away from the needle 40 distal end 44 (e.g., extending out of the lumen 43). Likewise, when the actuators 34a, 34b are slid or otherwise moved toward the handle assembly 18 into a disengagement position, the wire 50 and the corresponding wire distal portion 54 retracts toward or into the needle 40 distal end 44 (e.g., into the lumen 43).

The wire distal portion or tip 54 is adapted and configured to engage with an anchor 16, as shown in FIGS. 15-18. The anchor 16 can be any fixating, or self-fixating, tissue anchor provided at ends of a sling implant 17 (e.g., mesh or other known tissue support structures). The anchors 16 of the implant 17 are adapted for attachment within or through target tissue of the pelvic region of a patient, including those disclosed herein and in the incorporated references.

Figure 15:
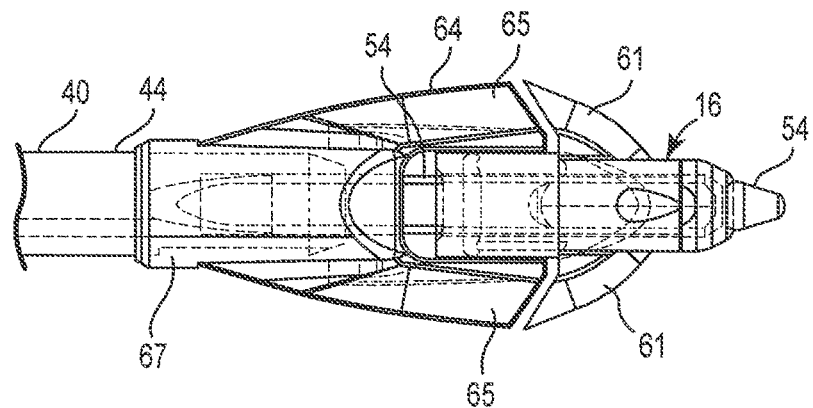
FIG. 15 is a top schematic view of a distal needle portion, wire tip and anchor device in accordance with embodiments of the present invention.

In the extended position, the wire distal portion 54 can be slid or snapped into engagement with the anchor 16. The anchor 16 and/or the wire distal portion 54 can include features to facilitate engagement and retention of the anchor 16 until the wire distal portion 54 is retracted away from engagement with the anchor 16. In one embodiment, the wire distal portion 54 is shaped and sized (e.g., tapered, bulbous, etc.) to extend into an internal channel or bore 60 within the anchor 16 for forceable or otherwise mateable engagement with the anchor 16. At least a portion of the wire distal portion 54 can be extendable out a distance from the engaged anchor 16 (FIG. 15). Upon retraction of the actuators 34a, 34b, and correspondingly the wire distal portion 54, the anchor 16 is generally freed of engagement with the needle 40 and its components. Other embodiments configured to facilitate selective engagement of the anchor 16 with the wire distal portion 54 or needle distal end 44 are disclosed in greater detail herein.

Figure 16:
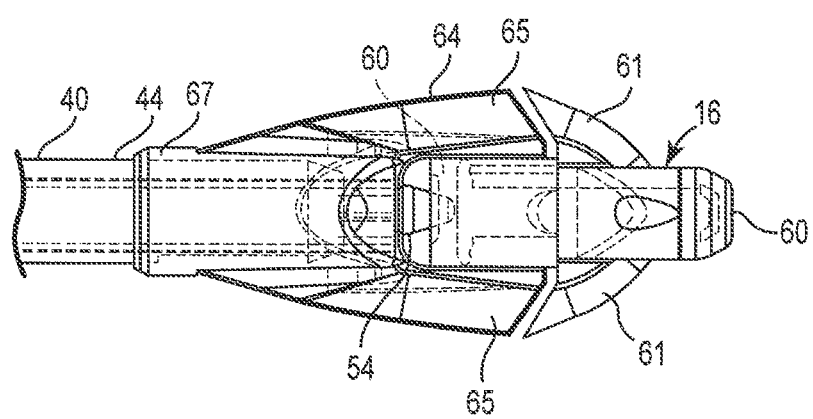
FIG. 16 is a top schematic view of a distal needle portion, wire tip and anchor device in accordance with embodiments of the present invention.

The needle assembly 40 can further include a barb guard 64 provided proximate the distal end 44, as depicted in FIGS. 15-16. The barb guard 64 can include a coupling portion 67 and one or more extending members 65. The barb guard 64 can be shaped and configured to interface with extending tines 61 of the anchor 16. For instance, the barb guard 64 can include one or more extending members 65. The extending members 65 can be straight, curved, flared and/or angled, or can take on a myriad of other compatible configurations. The barb guards 64 can prevent the tines 61 from engaging tissue until the wire distal portion 54 is disengaged from the anchor 16, and can provide an abutment surface for the anchor 16 when the wire distal portion 54 is retracted or pulled back to disengage the anchor 16 with activation of the one or more actuators 34a, 34b.

Figure 4:
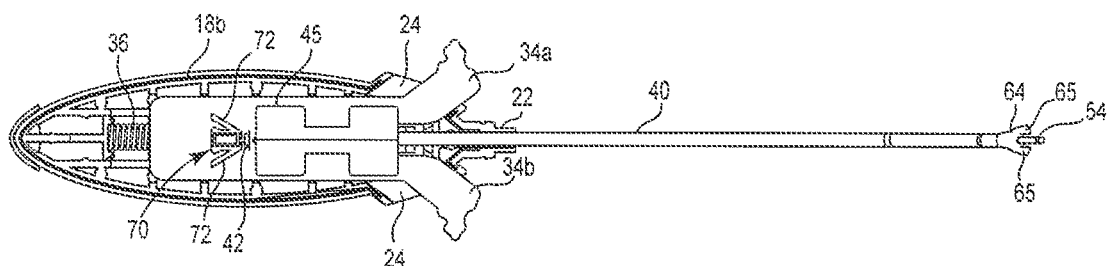
FIG. 4 is a schematic view of a surgical introducer needle and anchor system, with a lock-out assembly, in accordance with embodiments of the present invention.
Figure 5:
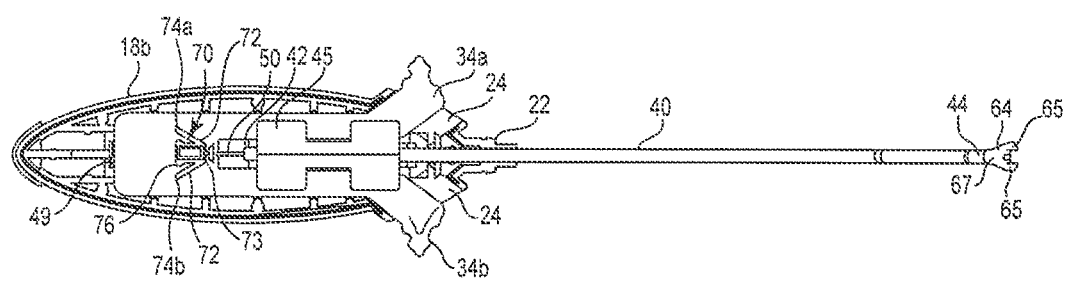
FIG. 5 is a schematic view of a surgical introducer needle and anchor system, with a lock-out assembly, in accordance with embodiments of the present invention.
Figure 5A:
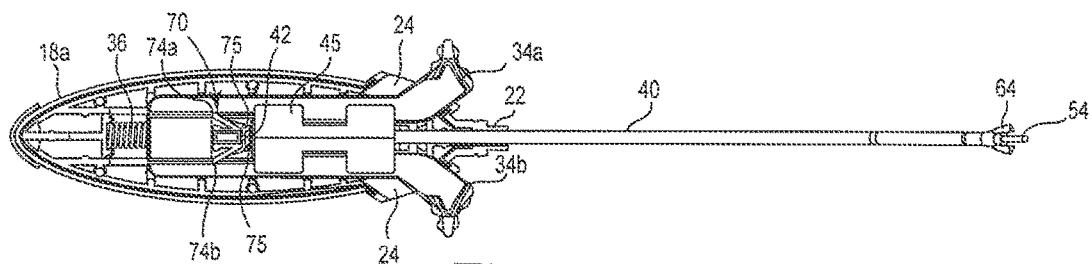
FIG. 5a is a schematic view of a surgical introducer needle and anchor system, with a lock-out assembly, in accordance with embodiments of the present invention.
Figure 5B:
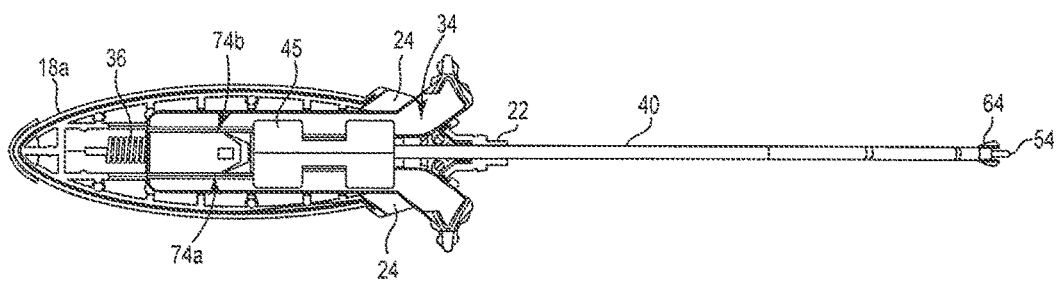
FIG. 5b is a schematic view of a surgical introducer needle and anchor system, with a lock-out assembly, in accordance with embodiments of the present invention.

In one embodiment, as shown in FIGS. 4-5b, the handle assembly 18 includes a lock-out assembly 70. The lock-out assembly 70 generally provides a feature in the handle 80 adapted to resist retraction or back travel of the distal tip 54 during deployment, or until the actuators 34a, 34b are engaged to retract the tip 54. Such a feature can be beneficial to keep the tip 54 from retracting during docking of the anchor 16 onto the tip 54. Further, such a feature can be beneficial in those procedures where the tip 54 may come into forceable contact with bone, device or implant structures, or other solid or unforgiving surfaces, thereby preventing the tip 54 from retracting until deployment of the anchor 16 is intended.

The lock-out assembly 70 can include a body portion 71 and an abutment feature 75. The body portion 71 includes one or more wing members 72. In one embodiment, the wing members 72 flare out at an angle, with wing tips 74a, 74b defined at ends of the members 72. The wing members 72 can be constructed of a material, e.g., polymer or metal, with at least a measurable level of flexibility such that the wing members 72 can deform, bend, pivot or otherwise move at least a small distance in toward the body portion 71. The abutment feature 75 can be defined by one or more wall portions provided with, or a recess provided within, the alignment portion 45, such as the proximal base 37 (FIG. 5a). The walls of the feature 75 can be angled in proximity to the positioned wing members 72. As such, the body portion 71 is seated within or adjacent the abutment feature 75. Further, the wing tips 74a, 74b extend out from a portion or surface of the alignment portion 45 to engage corresponding structures in at least one of the handle portions 18a, 18b (FIG. 5b). For instance, the wing tips 74a, 74b can be sized and shaped to engage notches, grooves or other structures in the handle portions 18a, 18b.

In an initial seating position, where the tip 54 is extended from the needle 40, the body portion 71 is seated within the abutment feature 75, the wing members 72 are relaxed or fully extended, and the wing tips 74a, 74b are engaged with respective portions of the handle 18. In this initial position, pressure on the needle tip 54, without engagement of the actuators 34a, 34b, will be resisted to generally prevent back travel or retraction. Namely, the wing tips 74a, 74b resist movement backward according to their seated position within the mating structure of the handle 18 and, therefore, the operatively coupled distal tip 54 will not retract. However, upon engagement of the actuators 34a, 34b toward the handle 18, the alignment portion 45 will begin moving which, in turn, moves the included abutment feature 75 surrounding the body portion 71. As a result, the angled walls of the feature 75 will begin to contact the wing members 72. This pressure on the wing members 72 will cause them to at least slightly deform or bend inward so that the wing tips 74a, 74b likewise move inward until the point where they release from the structures in the housing 18 where they were initially seated or secured. With the tips 74a, 74b released from a secured position, the actuators 34a, 34b are free to move, along with the corresponding body 35 and base 37 portions of the actuators, to retract the operatively coupled distal tip 54.

Figure 3:
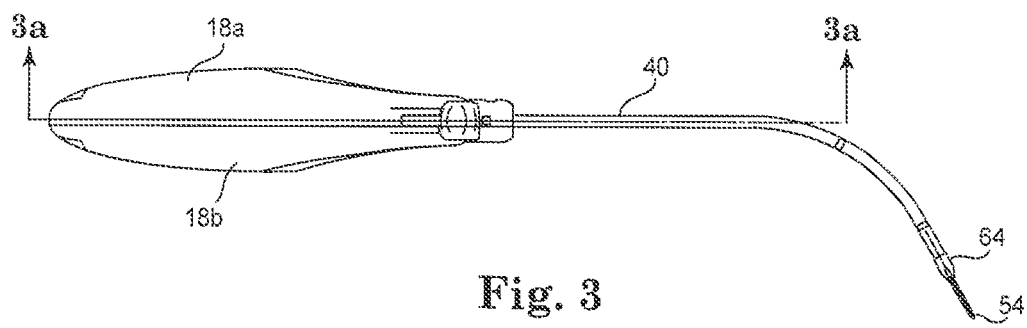
FIG. 3 is a side view of a surgical introducer needle and anchor system in accordance with embodiments of the present invention.
Figure 3A:
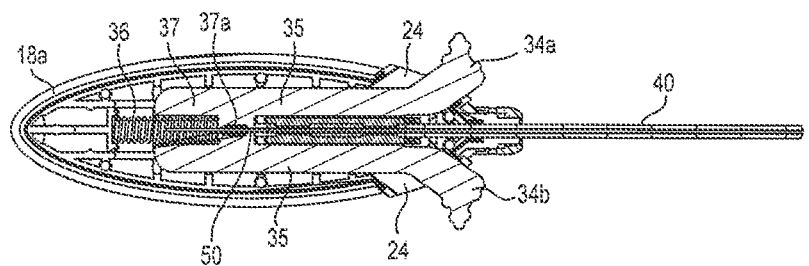
FIG. 3a is a schematic cross-section view of the surgical introducer needle and anchor system at line 3a-3a of FIG. 3.

Other embodiments of the system 10, such as that depicted in FIG. 3a, can be constructed without the lock-out assembly 70 described herein.

Figure 14:
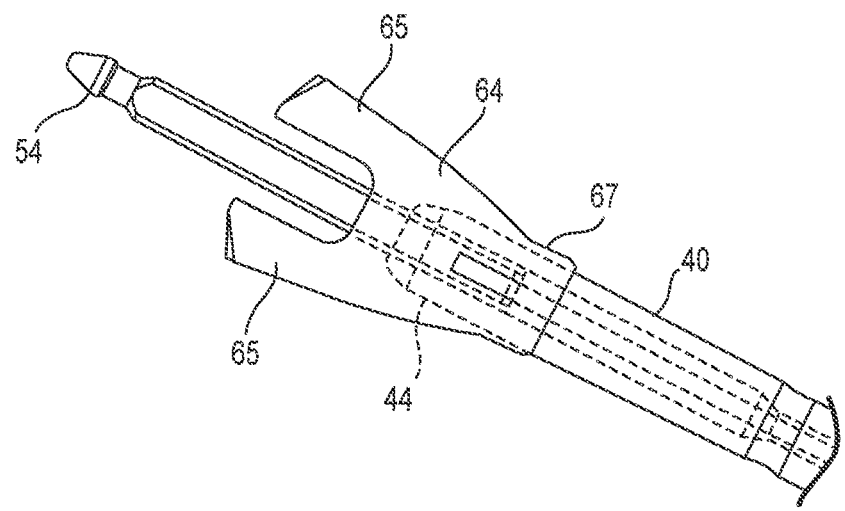
FIG. 14 is a schematic view of a distal needle portion and wire tip in accordance with embodiments of the present invention.
Figure 17:
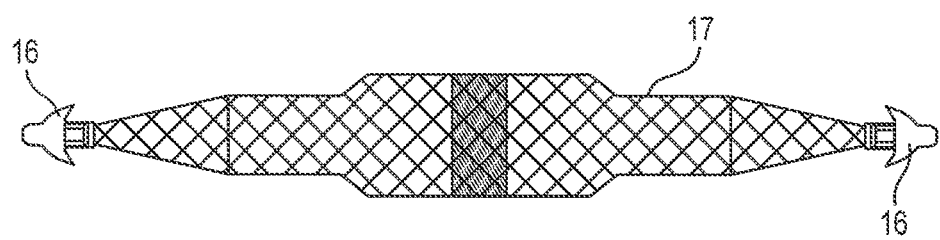
FIG. 17 is a top schematic view of a sling implant with end anchor devices in accordance with embodiments of the present invention.
Figure 18:
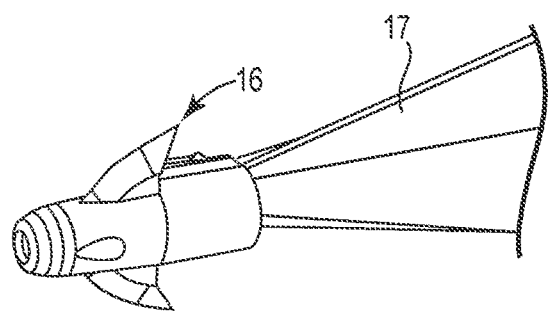
FIG. 18 is a schematic view of a sling implant coupled with an end anchor device in accordance with embodiments of the present invention.

In general use, the actuators 34a, 34b of the handle assembly 40 can initially be in an extended or engageable position such that the wire distal portion 54 is also in an extended/engageable position (FIGS. 3-4 and 14). As such, the anchor 16, e.g., a soft tissue anchor, can be inserted, fitted, snapped, or otherwise coupled to the distal end 54 (FIG. 15). As stated, a mesh, sling or support device or structure 17 can be connected with the tissue anchor 16 (FIGS. 17-18). The needle 40, distal end 54 and tissue anchor 16 are inserted into the pelvic region of a patient to a target tissue location where the anchor 16 can be inserted into or through the target tissue. The user can then activate or engage the actuators 34a, 34b to slide the actuators toward the handle assembly 18 (FIG. 5). This, in turn, compresses the biasing member 36 and causes the wire 50 to retract such that the distal portion 54 correspondingly withdraws (FIGS. 5 and 16). In certain embodiments, activation of the actuators 34a, 34b further disengages the lock-out assembly 70 to permit retraction of the distal portion 54 (FIGS. 5a-5b). At a point in the retraction, the distal portion 54 withdraws through the anchor bore 60, thereby disengaging or pulling away from the anchor 16, leaving the anchor 16 in the target tissue with the mesh, sling or other support device 17 or structure anchored. An audible click or reverb in the handle 18 can provide an indication to the user that the anchor 16 and wire distal portion 54 are disengaged. This process can be repeated for multiple anchor 16 insertions and target tissue anchoring procedures.

Other embodiments of the system 10 can include a clicker or toggle mechanism 80 adapted to selectively extend and retract the wire distal portion 54 within the needle 40. For instance, the toggle mechanism 80 can be operatively coupled to the handle assembly 18 and needle assembly 16.

The toggle mechanism 80 can include a housing 82 and an actuator 84, with the toggle mechanism 80 being provided with, and at least partially housed within, the handle assembly 18. The mechanism 80 can be configured in accordance with other embodiments described herein, wherein the mechanism 80 serves to replace the actuators 34a, 34b such that activation of the actuator 84 controls respective extension and retraction of the wire distal portion 54. In such an embodiment, the needle 20, wire 50, and handle 18 components from previously-detailed embodiments can be employed, all or in part.

The toggle mechanism 80 employed with various embodiments of the present invention can resemble or simulate known rotational locking mechanism implemented in various writing pen products. For instance, pressing of the actuator 84 causes an operatively coupled member (e.g., needle 90) to toggle between an extended and retracted position.

Figure 19:
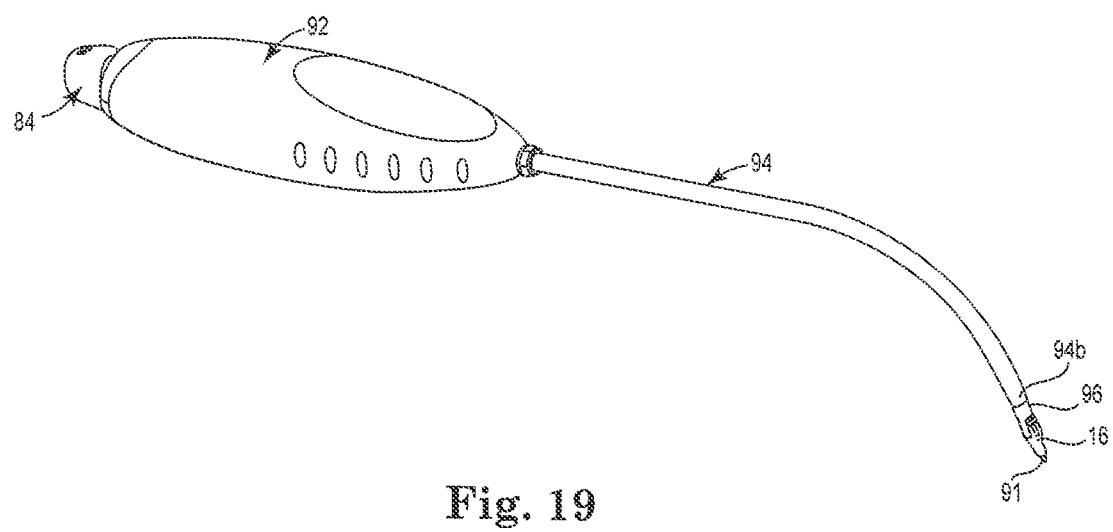
FIG. 19 is a perspective view of a surgical introducer needle and anchor system having a toggle mechanism in accordance with embodiments of the present invention.
Figure 20:
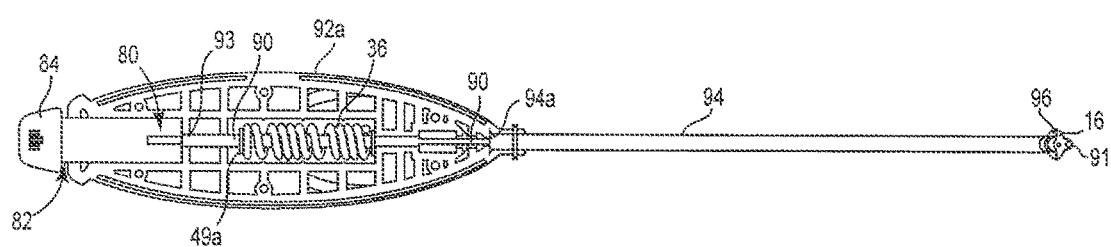
FIG. 20 is a schematic view of a surgical introducer needle and anchor system having a toggle mechanism in accordance with embodiments of the present invention.
Figure 21:
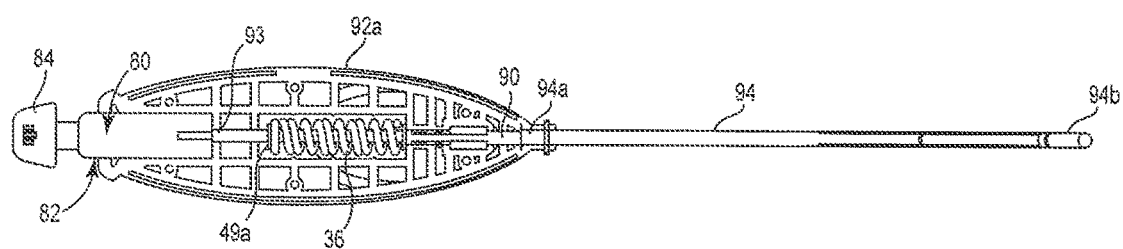
FIG. 21 is a schematic view of a surgical introducer needle and anchor system having a toggle mechanism in accordance with embodiments of the present invention.

Other embodiments employing a toggle mechanism, as shown in FIGS. 19-21, can resemble that of the previous embodiments described herein. However, these embodiments can include a generally solid needle 90 (e.g., rather than hollow), a handle assembly 92 and a tubular member 94. The handle assembly 92 can be provided in a clam shell configuration to define two handle portions 92a, 92b. The handle assembly 92 can further include a spring 36, operatively coupled with the toggle mechanism 80. The needle 90 extends from a distal end or tip 91 to a proximal end 93 operatively coupled to the toggle mechanism 80. The needle 90 can include a washer 49a attached thereto and adapted to abut a proximal end of the spring 49, with the needle 90 extending through the spring 49.

The tubular member 94 is configured to cover or surround the portion of the needle 90 extending out from the handle assembly 92. A proximal end 94a of the tubular member 94 is disposed within the handle assembly 92 to secure it in a generally stationary position, with the needle 90 slidable within the tubular member 94. The tubular member 94 can include a barb guard 96 at its distal end 94b, with the distal end 91 of the needle 90 adapted to extend out from and retract into the distal end 94b.

In general use of certain toggle mechanism embodiments, the needle tip 91 is initially in an extended/engageable position (FIGS. 19-20). As such, the anchor 16, e.g., a soft tissue anchor, can be inserted, fitted, snapped, or otherwise coupled to the tip 91 (FIG. 19). As stated, a mesh, sling or support device or structure 17 can be connected with the tissue anchor 16 (FIGS. 17-18). The needle 90, tip 91, and tissue anchor 16 are inserted into the pelvic region of a patient to a target tissue location where the anchor 16 can be inserted into or through the target tissue. The user can then activate or engage the actuator 84 (e.g., clicker or toggle button) which, in turn, causes the needle 90 to retract to decompress the biasing member 36. This decompression further withdraws the needle tip 91 from its initial extended position (FIG. 21, shown without the barb guard). At a point in the retraction, the tip 91 withdraws through the anchor bore 60, thereby disengaging or pulling away from the anchor 16, leaving the anchor 16 in the target tissue with the mesh, sling or other support device 17 or structure anchored. An audible click or reverb in the handle 92 can provide an indication to the user that the anchor 16 and needle tip 91 are disengaged. This process can be repeated for multiple anchor 16 insertions and target tissue anchoring procedures.

Various surgical introducer needle and anchor systems disclosed herein, otherwise known and/or previously incorporated by reference, can include various mechanisms, features or devices configured to provide increased reliability and usefulness in retaining and releasing an implant anchor. Various embodiments of the anchor systems of the present invention can include hard stop wedge devices, cut-away snap fit devices, split needle tip wedge devices, tube and wedge lock devices, locking barb devices, snap fit devices, squeeze-lock devices, limited press fit devices, one-sided and regional press fit devices, and the like devices or configurations.

Exemplary anchor systems 100, as generally illustrated in FIGS. 22-39, can include an anchor 101 having an internal channel or bore 102 extending from a proximal end 104 toward a distal end 106 along at least a portion of the total longitudinal length of the anchor 101. The internal channel 102 is capable of receiving a distal end (e.g., needle or wire tip) of an elongate needle 110 of an insertion tool to allow the anchor, such as a self-fixating tip, to be pushed into position within pelvic tissue during an implant procedure. Such anchor systems 100 provide security so that the anchor 101 will not easily detach or disengage from the needle during insertion, while still allowing for accurate placement and detachment of the anchor from the needle during deployment of the anchor, e.g., within soft tissue within the pelvic region of a patient.

Figure 22:
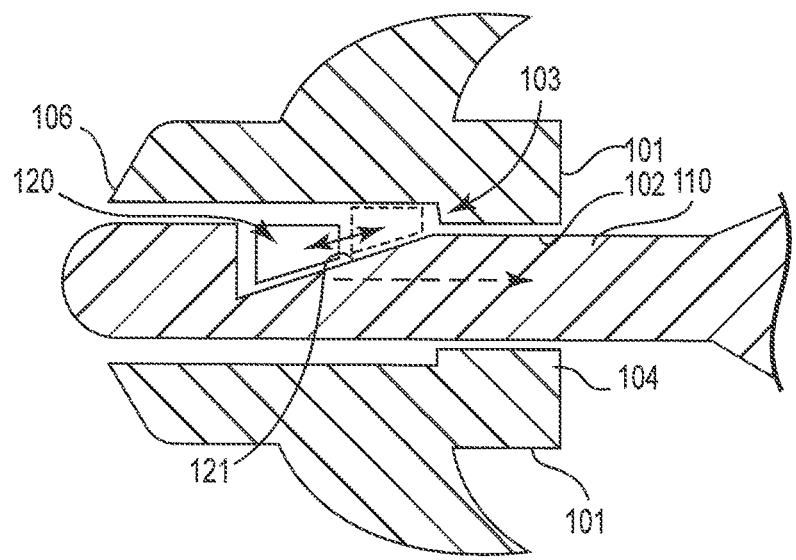
FIG. 22 is a schematic cross-section view of a wedge fit needle and anchor system in accordance with embodiments of the present invention.

FIG. 22 depicts an embodiment of the anchor system 100 having a hard stop and wedge feature 120 adapted to interlock the needle 110 and the anchor 101 for selective engagement and disengagement. The anchor 101 can include an abutment surface 103. The wedge 120 slides within a corresponding indent or notched travel path 121 within the needle 110 to create a hard stop interference to hold the anchor 101 in place and provide for selective release upon activation. The wedge 120 can be operatively coupled to the needle, a wire disposed within the needle, or to the anchor, for corresponding sliding to facilitate engagement/disengagement of the needle 110 with the anchor 101. In various embodiments, the needle instrument can be constructed of stainless steel or other compatible materials, while the anchor can be constructed of various materials, such as polypropylene, biocompatible metals, ceramics, polymers in general and resorbable polymers.

Figure 23:
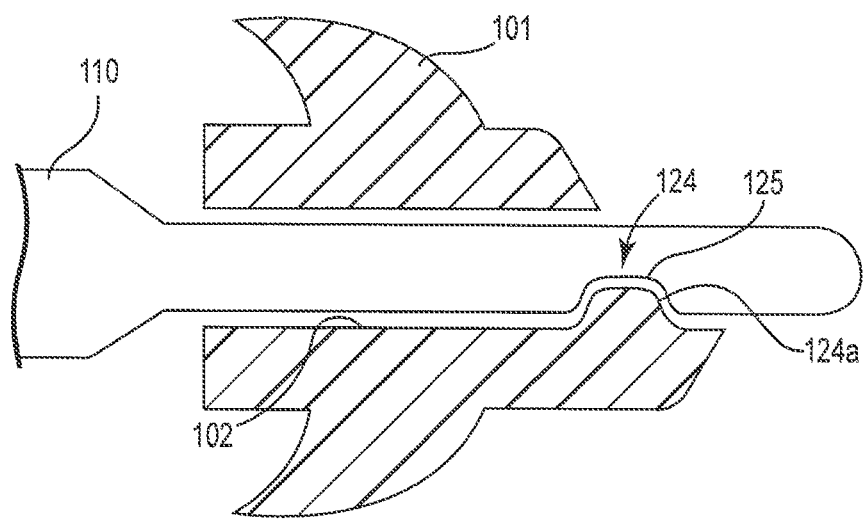
FIGS. 23-24 are schematic cross-section views of a snap fit needle and anchor system in accordance with embodiments of the present invention.
Figure 24:
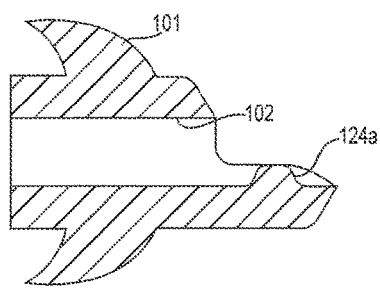

FIGS. 23-24 depict an embodiment of the anchoring system 100 having a cut-away snap fit feature 124 adapted to interlock the needle 110 and anchor 101 for selective engagement and disengagement. The feature 124 can include a protrusion 124a along a portion of the anchor 101 or bore 102 capable of snap engagement with a corresponding indent or notch 125 in the needle 40. FIG. 24 depicts an embodiment of the feature 124, with the protrusion 124a provided a distance from the distal tip of the anchor 101 to create more flex and thereby facilitate snap engagement.

Figure 25:
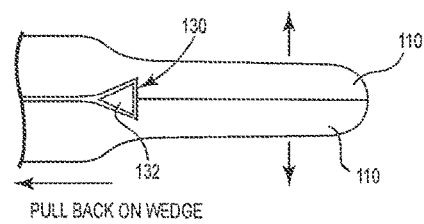
FIGS. 25-26 are schematic views of a split tip and wedge needle and anchor system in accordance with embodiments of the present invention.
Figure 26:
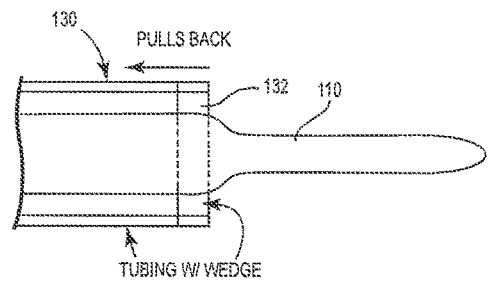

FIGS. 25-26 depict an embodiment of the anchoring system 100 having a split needle tip 110 and wedge feature 130 adapted to interlock the needle 110 and anchor 101 for selective engagement and disengagement. This embodiment can include a needle 110 with a split therealong and a slidable wedge 132 provided such that pulling back on the wedge spreads the needle proximate its distal end. This, in turn, spreads the end of the needle 110 to hold the anchor 101 in place. Reversal of the steps can likewise release the hold on the anchor 101, allowing selective release of the anchor from the needle. The wedge 132 can be operatively coupled to a pull device in the system, including a wire, suture, or other coupled member.

Figure 27:
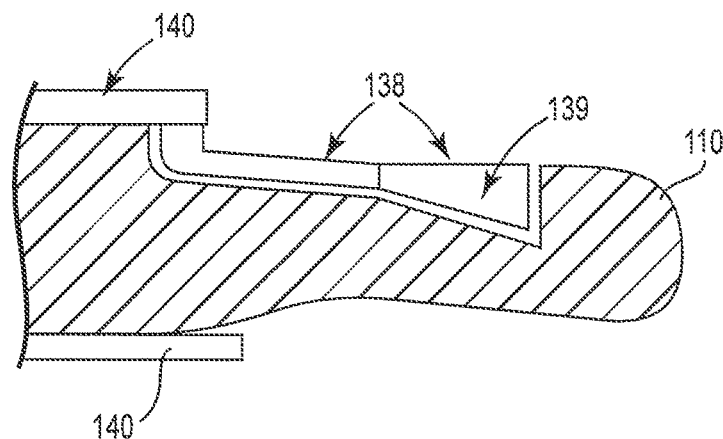
FIGS. 27-28 are schematic views of a tube and wedge lock needle and anchor system in accordance with embodiments of the present invention.
Figure 28:
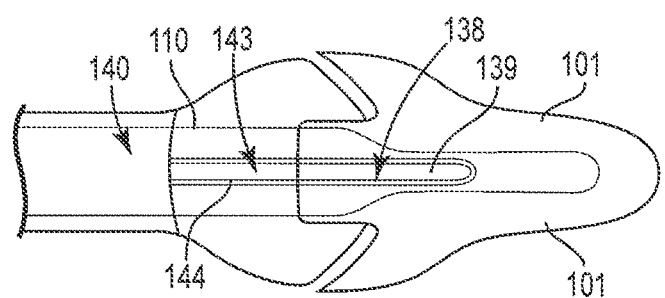

FIGS. 27-28 depict an embodiment of the anchoring system 100 having a tube and wedge feature 138 adapted to interlock the needle 110 and anchor 101 for selective engagement and disengagement. The wedge 139 is attached or otherwise provided along a portion of a tubing member 140, as part of the needle system 110. As such, relative movement of the needle 110 to the tubing 140 drives the movement of the wedge 139 in a groove 141 of the needle 110. This movement of the wedge 139 provides for selective engagement of the anchor 101 with the needle 110. An attachment member 143 can couple the tubing 140 and the wedge 139 to facilitate movement of the wedge 139. Further, the attachment member 143 can reside and/or travel in a groove 144.

FIGS. 29a-31b depict an embodiment of the anchoring system 100 having a locking barb and guard feature 148 adapted to interlock the needle 110 and anchor 101 for selective engagement and disengagement. The barb feature 148 can include barbs or tabs 150, or other protrusions, along a distal portion of the needle 110, with the barbs 150 adapted to selectively engage corresponding indent features 151 in the anchor 101 for selective engagement of the anchor 101 with the needle 110. Other variations on the barb and guard feature 148 are disclosed as well. For instance, the embodiments of FIGS. 31a-31b can further include a relatively flexible guard feature 148 tending to remain in an open position (FIG. 31a). A tube member 152 can be included such that when the tube 152 is slid forward, the barb guard feature is moved into a closed position to engage the barbs 150 with the anchor indents 151 or other portions of the anchor (FIG. 31b), FIGS. 32a-32c depict an embodiment of the anchoring system 100 having a snap fit feature 156 adapted to interlock the needle 110 and anchor 101 for selective engagement and disengagement. The anchor 101 can include protrusions 158, tabs, or like features adapted to engage with corresponding indent or groove features 160 in the needle 110. Alternatively, the protrusions 158 can be provided along a portion of the needle 110, with the anchor 101 including engageable indent or groove features 160. Other variations on the snap fit feature 156 are disclosed as well, where the protrusions 158 in the anchor 101 or provided or formed through a molding process (e.g., formation with a core pin and/or with a mold portion or half).

FIGS. 33-34 depict an embodiment of the anchoring system 100 having a squeeze lock feature 164 adapted to interlock the needle 110 and anchor 101 for selective engagement and disengagement. The squeeze lock feature 164 can include a wire 166, or other mechanism, such that the tip of the needle 110 expands under applied tension. This expansion provides a hold on the anchor 101 (FIG. 34). When the tension is released, the needle tip returns to its relaxed state, allowing the anchor 101 to slide off of the needle 110 (FIG. 33).

Figure 35:
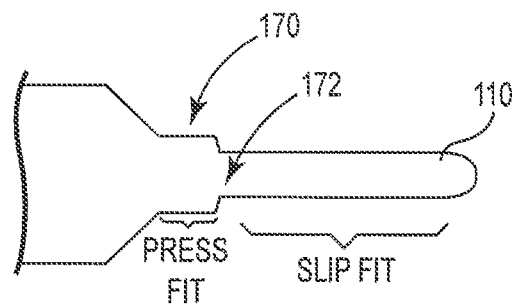
FIG. 35 is a schematic view of a limited press fit needle and anchor system in accordance with embodiments of the present invention.

FIG. 35 depicts an embodiment of the anchoring system 100 having a limited press fit feature 170 adapted to interlock the needle 110 and anchor 101 for selective engagement and disengagement. The limited press fit feature 170 can be limited to structure, e.g., a step feature 172, along a limited or predefined length of the needle 110. As such, an end length of the distal needle tip 110 can be sized to provide for a slip flit within the anchor 101, while another predefined length or feature 172 includes a slightly larger diameter or width to provide press fitting with the anchor 101. This, in turn, allows for selective engagement of the anchor 101 with the needle 110.

Figure 36:
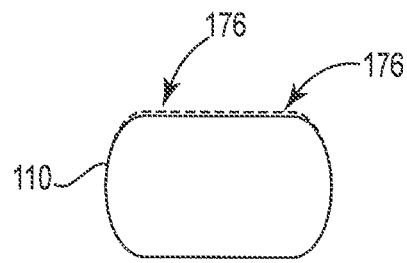
Figure 37:
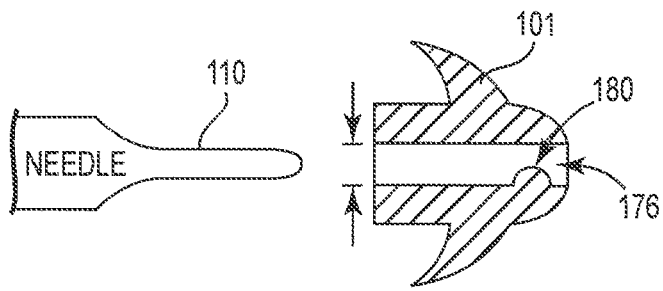
FIGS. 37-38 are schematic views of one-sided and regional press fit needle and anchor systems in accordance with embodiments of the present invention.
Figure 38:
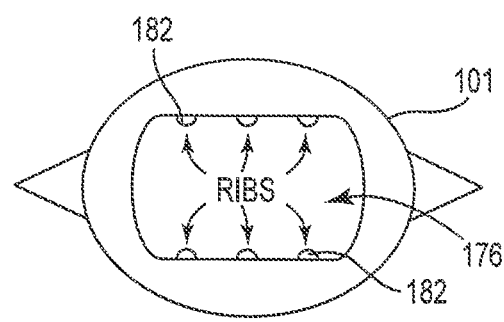

FIGS. 36-38 depict an embodiment of the anchoring system 100 having a press fit feature 176 adapted to interlock the needle 110 and anchor 101 for selective engagement and disengagement. In one embodiment, the press fit feature 176 is limited to one side or region of the needle 110 such that the added thickness creates a press fit when engaged with the internal channel 102 of the anchor 101. Other variations of the press fit feature are disclosed as well, including internal ribs 182 and other structures 180 within the anchor channel to provide for selective engagement of the anchor 101 with the needle 110. In FIG. 36, for instance, the press fit feature 176 is provided only on one side or region of the needle 110, rather than around the needle 110 circumference. FIG. 37 discloses a press fit feature 176 including a protrusion or tab 180 provided within the internal channel 102 of the anchor to facilitate press fitting to the needle 110. FIG. 38 discloses a press fit feature 176, wherein the internal channel 102 of the anchor 101 includes a plurality of ribs 182 to facilitate press fitting to the needle 100.

The systems 10, 100 and their various components, structures, features, materials and methods may have a number of suitable configurations as shown and described in the previously-incorporated references.

A variety of materials may be used to form portions, structures or components of the systems 10, 100 described herein, including nitinol, polymers, elastomers, thermoplastic elastomers, metals, ceramics, springs, wires, plastic tubing, and the like.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

The invention claimed is:
1. A surgical needle system, comprising:
an anchor device including a first tine and a second tine;
a needle including a proximal end portion and a distal end portion, the first tine and the second tine of the anchor device abuttably seatable against the distal end portion, the needle defining a lumen; and
a handle assembly including a first actuator and a second actuator, the first actuator and the second actuator being coupled by a base portion, an alignment member disposed inside of the handle assembly, and a body portion having a proximal portion and a distal portion, the distal portion of the body portion coupled to the proximal end portion of the needle, the needle being configured to engage the alignment member to align and secure the proximal end of the needle within the handle assembly;
a connecting member having a proximal end and a distal end, the proximal end of the connecting member coupled to the base portion, the distal end of the connecting member configured to extend out of the lumen at the distal end portion of the needle in response to the at least one actuator being within an extended position, the anchor device defining an anchor bore configured to receive and engage with the distal end of the connecting member,
wherein the first actuator and the second actuator are configured to proximally retract along the body portion causing the connecting member to retract and the distal end of the connecting member to withdraw from the anchor bore.

2. The system of claim 1, wherein the distal end portion of the needle includes a barb guard.

3. The system of claim 1, wherein the first and second actuators extend out angularly from an outer surface of the body portion of the handle assembly.

4. The system of claim 1, wherein the distal end portion of the needle includes a curved length.

5. The system of claim 1, wherein the connecting member includes a wire.

6. The system of claim 5, wherein the anchor bore of the anchor device is engageable with a distal end portion of the wire.

7. The system of claim 1, further including a sling implant, with the anchor device provided with the sling implant.

8. The system of claim 1, wherein the distal end portion of the needle includes a barb guard, the barb guard including a coupling portion, a first extending member, and a second extending member, the first extending member having a first terminal end coupled to the coupling portion and a second terminal end configured to engage with a terminal end of the first tine.

9. The system of claim 1, wherein each of the first actuator and the second actuator includes a body portion to define a gap therebetween.

10. The system of claim 9, wherein the alignment member is configured to be disposed within the gap.

11. The system of claim 1, wherein the alignment member includes a H-shaped block.

12. A surgical needle system, comprising:
an anchor device including a first tine and a second tine;
a needle including a proximal end portion and a distal end portion, the distal end portion including a barb guard, the barb guard including a first flared extension and a second flared extension, wherein a terminal end of the first flared extension and a terminal end of the second flared extension is configured to contact a terminal end of the first tine and a terminal end of the second tine, respectively;
a handle assembly including at least one actuator, and a body portion having a proximal portion and a distal portion, the distal portion of the body portion coupled to the proximal end portion of the needle; and
a wire having a proximal end and a distal end, the proximal end of the wire coupled to the at least one actuator, the distal end of the wire configured to extend out of a lumen at the distal end portion of the needle in response to the at least one actuator being within an extended position, the anchor device defining an anchor bore configured to receive and engage with the distal end of the wire,
wherein the at least one actuator is configured to proximally retract along the body portion causing the wire to retract and the distal end of the wire to withdraw from the anchor bore,
wherein the handle assembly further includes a spring biasing the wire outwardly.

13. The system of claim 12, wherein the at least one actuator includes a first actuator and a second actuator.

14. The system of claim 13, wherein the first and second actuators extend out angularly from an outer surface of the body portion of the handle.

15. The system of claim 12, wherein the distal end portion of the needle includes a curved length.

16. The system of claim 12, wherein the anchor bore of the anchor device is engageable with a distal end portion of the wire.

17. The system of claim 12, further including a sling implant.

18. The system of claim 17, wherein the anchor device is provided with the sling implant.

19. A surgical needle system, comprising:
an anchor device including a first tine and a second tine;
a needle including a proximal end portion and a distal end portion, the first tine and the second tine of the anchor device abuttably seatable against the distal end portion, the needle defining a lumen; and
a handle assembly including at least one actuator, and a body portion having a proximal portion and a distal portion, the distal portion of the body portion coupled to the proximal end portion of the needle;
a wire having a proximal end and a distal end, the proximal end of the wire coupled to the at least one actuator, the distal end of the wire configured to extend out of the lumen at the distal end portion of the needle in response to the at least one actuator being within an extended position, the anchor device defining an anchor bore configured to receive and engage with the distal end of the wire,
wherein the at least one actuator is configured to proximally retract along the body portion causing the wire to retract and the distal end of the wire to withdraw from the anchor bore, and
wherein the handle assembly includes a spring biasing the wire outwardly.

* * * * *